(12) United States Patent
Sommer et al.

(10) Patent No.: US 7,871,820 B2
(45) Date of Patent: Jan. 18, 2011

(54) HIGH FREQUENCY OF NEUREXIN 1β SIGNAL PEPTIDE STRUCTURAL VARIANTS IN PATIENTS WITH AUTISM

(75) Inventors: Steve S. Sommer, Duarte, CA (US); Jinong Feng, Arcadia, CA (US); Jin Yan, Duarte, CA (US)

(73) Assignee: City of Hope, Duarte, CA (US)

( * ) Notice: Subject to any disclaimer, the term of this patent is extended or adjusted under 35 U.S.C. 154(b) by 552 days.

(21) Appl. No.: 11/859,631

(22) Filed: Sep. 21, 2007

(65) Prior Publication Data

US 2009/0197253 A1 Aug. 6, 2009

Related U.S. Application Data

(60) Provisional application No. 60/846,515, filed on Sep. 22, 2006.

(51) Int. Cl.
*C12P 19/34* (2006.01)
(52) U.S. Cl. .......................................... 436/6; 435/91.2
(58) Field of Classification Search ....................... None
See application file for complete search history.

(56) References Cited

PUBLICATIONS

Philippi et al. Molecular Psychiatry (2005) 10, 950-960.*
Sommer et al. (American Journal of Medical Genetics Part B: Neuropsychiatric Genetics; vol. 138B Issue 1, p. 70, (Sep. 5, 2005) Special Issue: XIII World Congress of Psychiatric Genetics 2005; Published Online Sep. 21, 2005).*
Print out from American Journal of Medical Genetics Part B website, accessed Apr. 19, 2010. 2 pages.*
GeneCard for Neurexin 1 Gene, obtained from http://www.genecards.org/cgi-bin/carddisp.pl?gene=Nrxn1 Apr. 19, 2010, ninteen pages.*
Buzin CH, Wen CY, Nguyen VQ, Nozari G, Mengos A, Li X, Chen JS, Liu Q, Gatti RA, Fujimura FK, Sommer SS. 2000. Scanning by DOVAM-S detects all unique sequence changes in blinded analyses: evidence that the scanning conditions are generic. BioTechniques 28:746-753.
Cook EHJ, Courchesne RY, Cox NJ, Lord C, Gonen D, Guter SJ, Lincoln A, Nix K, Haas R, Leventhal BL, Courchesne E. 1998. Linkage-disequilibrium mapping of autistic disorder, with 15q11-13 markers. Am J Hum Genet 62:1077-1083.
Dean C, Scholl FG, Choih J, DeMaria S, Berger J, Isacoff E, Scheiffele P. 2003. Neurexin mediates the assembly of presynaptic terminals. Nat Neurosci 6:708-716.
Garner CC, Nash J, Huganir RL. 2000. PDZ domains in synapse assembly and signalling. Trends Cell Biol 10:274-280.
Hortsch M, Meyer DI. 1986. Transfer of secretory proteins through the membrane of the endoplasmic reticulum. Int Rev Cytol 102:215-242.
Ichtchenko K, Hata Y, Nguyen T, Ullrich B, Missler M, Moomaw C, Sudhof TC. 1995. Neuroligin 1: a splice site-specific ligand for beta-neurexins. Cell 81:435-443.

Jamain S, Quach H, Betancur C, Rastam M, Colineaux C, Gillberg IC, Soderstrom H, Giros B, Leboyer M, Gillberg C, Bourgeron T. 2003. Mutations of the X-linked genes encoding neuroligins NLGN3 and NLGN4 are associated with autism. Nat Genet 34:27-29.
Kleiderlein JJ, Nisson PE, Jessee J, Li WB, Becker KG, Derby ML, Ross CA, Margolis RL. 1998. CCG repeats in cDNAs from human brain. Hum Genet 103:666-673.
Laumonnier F, Bonnet-Brilhault F, Gomot M, Blanc R, David A, Moizard MP, Raynaud M, Ronce N, Lemonnier E, Calvas P, Laudier B, Chelly J, Fryns JP, Ropers HH, Hamel BC, Andres C, Barthelemy C, Moraine C, Briault S. 2004. X-linked mental retardation and autism are associated with a mutation in the NLGN4 gene, a member of the neuroligin family. Am J Hum Genet 74:552-557.
Lobo-Menendez F, Sossey-Alaoui K, Bell JM, Copeland-Yates SA, Plank SM, Sanford SO, Skinner C, Simensen RJ, Schroer RJ, Michaelis RC. 2003. Absence of MeCP2 mutations in patients from the South Carolina autism project. Am J Med Genet B Neuropsychiatr Genet 117:97-101.
Missler M, Sudhof TC. 1998. Neurexins: three genes and 1001 products. Trends Genet 14:20-26.
Rowen L, Young J, Birditt B, Kaur A, Madan A, Philipps DL, Qin S, Minx P, Wilson RK, Hood L, Graveley BR. 2002. Analysis of the human neurexin genes: alternative splicing and the generation of protein diversity. Genomics 79:587-597.
Schroer RJ, Phelan MC, Michaelis RC, Crawford EC, Skinner SA, Cuccaro M, Simensen RJ, Bishop J, Skinner C, Fender D, Stevenson RE. 1998. Autism and maternally derived aberrations of chromosome 15q. Am J Med Genet 76:327-336.
Tabuchi K, Sudhof TC. 2002. Structure and evolution of neurexin genes: insight into the mechanism of alternative splicing. Genomics 79:849-859.
Ullrich B, Ushkaryov YA, Sudhof TC. 1995. Cartography of neurexins: more than 1000 isoforms generated by alternative splicing and expressed in distinct subsets of neurons. Neuron 14:497-507.
Ushkaryov YA, Hata Y, lchtchenko K, Moomaw C, Afendis S, Slaughter CA, Sudhof TC. 1994. Conserved domain structure of beta-neurexins. Unusual cleaved signal sequences in receptor-like neuronal cell-surface proteins. J Biol Chem 269:11987-11992.
von Heijne G. 1986. A new method for predicting signal sequence cleavage sites. Nucleic Acids Res 14:4683-4690.
Yan J, Oliveira G, Coutinho AM, Yang C, Feng J, Katz C, Sram J, Bockholt A, Jones IR, Craddock N, Cook EHJ, Vicente AM, Sommer SS. 2005. Analysis of the neuroligin 3 and 4 genes in autism and other neuropsychiatric patients. Molecular Psychiatry 10:329-332.

* cited by examiner

*Primary Examiner*—Juliet C Switzer
(74) *Attorney, Agent, or Firm*—Perkins Coie LLP; Lauren Sliger

(57) ABSTRACT

The three β-neurexins have similar roles in synaptogenesis and interact with the neuroligins. Mutations located within the gene encoding neurexin 1 have been identified as molecular markers associated with autism and autism-related disorders. The estimated attributable risk is 2%. The invention provides methods of diagnosing or predicting susceptibility to developing autism in an individual by determining the presence or absence of one or more genetic variant of a neurexin 1 gene in an individual.

6 Claims, 3 Drawing Sheets

Figure 1

NM_138735: NRXN1β

```
                                                    c.41C>T,p.S14L
   atgtaccagaggatgctccggtgcggcgccgagctgggctcgcccggggggcggcggcggc
 1 ---------+---------+---------+---------+---------+---------+
   tacatggtctcctacgaggccacgccgcggctcgacccgagcgggccccgccgccgccg MetTyrGlnArgMetLeuArgCysGlyAlaGluLeuGlySerProGlyGlyGlyGlyGly
    +---------------------------+----------------------------+-
    1                           10                           20 c.118A>T,p.T40S
   ggcggcggcggcggcggcgcaggggggcgcctggccctgctttggatagtcccgctcacc
61 ---------+---------+---------+---------+---------+---------+
   ccgccgccgccgccgccgcgtccccccgcggaccgggacgaaacctatcagggcgagtgg GlyGlyGlyGlyGlyGlyAlaGlyGlyArgLeuAlaLeuLeuTrpIleValProLeuThr
    ---------------------------+----------------------------+-
                                30                          40 ctcagcggcctcctaggagtggcgtgggggcatccagtttgggagcgcaccacatccac
121 ---------+---------+---------+---------+---------+---------+
    gagtcgccggaggatcctcaccgcacccccgtaggtcaaaccctcgcgtggtgtaggtg LeuSerGlyLeuLeuGlyValAlaTrpGlyAlaSerSerLeuGlyAlaHisHisIleHis
    ---------------------------+----------------------------+-
                                50                          60
```

[SEQ ID NO:1 & 2]

Figure 2

NRXN1β c.41C>T; p.S14L variant (bold) [SEQ ID NO:3 & 4]

```
    atgtaccagaggatgctccggtgcggcgccgagctgggcttgcccggggcggcggcggc
1   ---------+---------+---------+---------+---------+---------+
    Tacatggtctcctacgaggccacgccgcggctcgacccgagcgggccccgccgccgccg MetTyrGlnArgMetLeuArgCysGlyAlaGluLeuGlyLeuProGlyGlyGlyGlyGly
    +-------------------------+-------------------------+-
    1                         10                        20
    ggcggcggcggcggcggcgcaggggggcgcctggccctgctttggatagtcccgctcacc
61  ---------+---------+---------+---------+---------+---------+
    Ccgccgccgccgccgccgcgtcccccgcggaccgggacgaaacctatcagggcgagtgg GlyGlyGlyGlyGlyGlyAlaGlyGlyArgLeuAlaLeuLeuTrpIleValProLeuThr
    -------------------------+-------------------------+-
                             30                        40
    ctcagcggcctcctaggagtggcgtggggggcatccagtttgggagcgcaccacatccac
121 ---------+---------+---------+---------+---------+---------+
    Gagtcgccggaggatcctcaccgcacccccgtaggtcaaaccctcgcgtggtgtaggtg LeuSerGlyLeuLeuGlyValAlaTrpGlyAlaSerSerLeuGlyAlaHisHisIleHis
    -------------------------+-------------------------+-
                             50                        60
```

Figure 3

NRXN1β c.118A>T; p.T40S variant (bold) [SEQ ID NO:5 & 6]

```
     atgtaccagaggatgctccggtgcggcgccgagctgggctcgcccggggggcggcggcggc
1    ---------+---------+---------+---------+---------+---------+
     Tacatggtctcctacgaggccacgccgcggctcgacccgagcgggcccccgccgccgccg MetTyrGlnArgMetLeuArgCysGlyAlaGluLeuGlySerProGlyGlyGlyGlyGly
        +--------------------------+--------------------------+-
     1                             10                          20 ggcggcggcggcggcggcgcaggggggcgcctggccctgctttggatagtcccgctctcc
61   ---------+---------+---------+---------+---------+---------+
     Ccgccgccgccgccgccgcgtcccccgcggaccgggacgaaacctatcagggcgagagg GlyGlyGlyGlyGlyGlyAlaGlyGlyArgLeuAlaLeuLeuTrpIleValProLeuSer
     ---------------------------+--------------------------+-
                                 30                          40 ctcagcggcctcctaggagtggcgtggggggcatccagtttgggagcgcaccacatccac
121  ---------+---------+---------+---------+---------+---------+
     Gagtcgccggaggatcctcaccgcaccccccgtaggtcaaaccctcgcgtggtgtaggtg LeuSerGlyLeuLeuGlyValAlaTrpGlyAlaSerSerLeuGlyAlaHisHisIleHis
     ---------------------------+--------------------------+-
                                 50                          60
```

HIGH FREQUENCY OF NEUREXIN 1β SIGNAL PEPTIDE STRUCTURAL VARIANTS IN PATIENTS WITH AUTISM

PRIORITY CLAIM

This application claims priority to U.S. Provisional Application Ser. No. 60/846,515, filed Sep. 22, 2006, which is incorporated herein by reference.

BACKGROUND

Each of the references cited herein is incorporated by reference in its entirety. A complete listing of the citations is set forth at the end of the specification.

FIELD OF THE INVENTION

The invention relates generally to novel methods of diagnosing, preventing, and treating specific neurological disorders which are characterized by developmental disability. One such disease exemplified is autism or autism spectrum disorder. This invention relates to genetic predisposition to autism or autism related disorder.

Autism is a complex developmental disorder that generally presents in the first few years of life and is characterized by deficits in social interaction, behavior and communication. Recently, mutations in the neuroligin 3 (NLGN3, MIM #300336) and neuroligin 4 genes (NLGN4, MIM #300427) were identified in patients with autism or mental retardation [Jamain et al., 2003; Laumonnier et al., 2004; Yan et al., 2004; Schwarts 2006].

Neuroligins are postsynaptic membrane cell-adhesion molecules which bind to β-neurexins, a family of proteins that act as neuronal cell surface presynaptic receptors [Missler and Sudhof, 1998]. The three neurexin genes are designated NRXN1 (MIM#600565), NRXN2 (MIM#600566), and NRXN3 (MIM#600567). The neurexin genes have two independent promoters which generate 2 classes of mRNAs: the longer mRNAs encode a-neurexins and the shorter mRNAs encode β-neurexins [Ichtchenko et al., 1995]. The domain organization of α-neurexin is as follows: an N-terminal signal peptide, three "neurexin repeats", a carbohydrate attachment region, a transmembrane domain, and a short cytoplasmic domain. The neurexin repeats are composed of two LNS (lamanin/neurexin/sex hormone-binding globulin) domains (A and B) flanking an EGF like domain. The beta neurexins contain a different signal peptide, a short region unique to beta neurexins, the LNS [B] domain from the last neurexin repeat followed by the carbohydrate attachment region, the transmembrane and the cytoplasmic domains.

Neurexins display an evolutionarily conserved pattern of extensive alternative splicing. Multiple neurexin proteins can be generated from each of the genes. There are five sites of alternative splicing in the α-neurexin transcripts, two of which are shared with the β-neurexin transcripts. As a result, the total number of neurexins in brain probably exceeds 2,000 [Ullrich et al., 1995].

The human neurexin genes (NRXN1, 2, 3) span 1.1 Mb, 106 kb and 1.6 Mb, respectively [Tabuchi and Sudhof, 2002; Kleiderlein et al., 1998; Tabuchi and Sudhof, 2002]. The NRXN1 and NRXN3 genes have very large introns. The CpG rich promoter for β-neurexins is located downstream of exon 17 of the neurexin a genes [Rowen et al., 2002]. The NRXN1β, NRXN2β and NRXN3β transcripts contain 6, 6, and 7 exons, respectively, including 442, 666, and 432 amino acids, respectively.

The interaction of neuroligin and β-neurexin in cultured neurons induces morphological events resembling synapse formation [Garner et al., 2000], suggesting that neurexins function in the specification and/or initiation of synapse formation. Dean et al found that β-neurexin clustering was sufficient to trigger the recruitment of synaptic vesicles through interactions that require the cytoplasmic domain of neurexin [Dean et al., 2003].

Identification of markers which are closely associated with autism and autism related disorders would provide the basis for novel diagnostic tests which will augment current behavioral based methods of diagnosis. Structural variants in the β-neurexin genes that predispose an individual to autism were identified by scanning the three β-neurexin genes in patients with autism. Because diagnosis of autism is primarily based on methods assessing behavior in young patients, a genetic screening assay to assist in the diagnosis is of particular value especially to allow early diagnosis and thus, earlier intervention and therapy. A reliable genetic test for autism would also be useful for predicting susceptibility to autism in asymptomatic individuals, making prophylactic therapy possible. The present invention satisfies this need and provides related advantages as well.

SUMMARY OF THE INVENTION

The invention provides a method of diagnosing or predicting susceptibility to autism or an autism related disorder by determining the presence of one or more genetic variants of a neurexin 1 gene or neurexin β gene, where the presence of a structural variant indicates that the subject has or is predisposed to autism or an autism related disorder such as autism spectrum disorder.

BRIEF DESCRIPTION OF THE DRAWINGS

FIG. 1 shows the nucleotide and amino acid sequence of the neurexin-1 gene. The location of the variants p.S14L (c.41C>T) and p.T40S (c.118A>T) are indicated. NM_138735 [SEQ ID NO:1].

FIG. 2 shows the nucleotide and amino acid sequence of the neurexin-1β gene for the p.S14L variant [SEQ ID NO:4]. The location of the c.41 C>T [SEQ ID NO:3] missense is underlined.

FIG. 3 shows the nucleotide sequence of the neurexin-1β gene for the p.T40S variant [SEQ ID NO:6]. The location of the c.118 A>T [SEQ ID NO: 5] missense is underlined.

DETAILED DESCRIPTION

The present invention relates to the identification of genetic markers associated with autism and autism related disorders. These genetic sequence variants of the neurexin 1 gene and neurexin-1β gene show relevance as markers of autism and can be used to diagnose or predict susceptibility to autism and autism related disorders. Such structural variants are located, for example, in exon 1 of the neurexin-1β gene. Additional structural variants are located in exons 7, 9, 10 and/or 13 of the neurexin 1 gene.

As disclosed herein, the neurexin genes of patients diagnosed with autism were scanned for mutations in the neurexin 1β, 2β and 3β genes. In particular, two allelic variants p.S14L [SEQ ID NO:4;] (c.41C>T) [SEQ ID NO:3] and p.T40S [SEQ ID NO:6]; (c.118A>T) [SEQ ID NO: 5] consisting of missense mutations in exon 1 of neurexin-1β were identified and demonstrated to be associated with autism. These results indicate that the presence of neurexin-1β gene variants can be used as genetic markers to diagnose or predict susceptibility to autism or an autism related disorder.

In addition, the neurexin genes of patients diagnosed with autism were scanned for mutations in the neurexin 1 gene. The neurexin 1 gene consists of 24 exons. Neurexin 1 alpha is composed of exons 1 thru 24. Neurexin 1 beta is a carboxy terminal segment of neurexin alpha. It contains exons 18 thru 24 plus an alternatively spliced exon located in intron 17 of the neurexin alpha gene. Several variants were identified. The variants included missense mutations and nucleotide base changes in exons 1, 7, 9, 10 and 13. In particular, variants having amino acid changes at positions 8, 13, 28, 53, 250, 429, 665, 715, 869, 620, 679, 713, and 730 were identified and demonstrated to be associated with autism (See Table 4). Thus, the presence of neurexin 1 gene variants can be used as a genetic marker to diagnose or predict susceptibility to autism or an autism related disorder.

Based on the above findings, the present invention provides methods of diagnosing or predicting susceptibility to autism or an autism related disorder such as autism spectrum disorder by determining the presence or absence of a neurexin-1β gene or neurexin-1 gene variant where the presence of an allelic variant indicates that the subject has or is at increased risk of developing autism or an autism related disorder. Neurexin 2β and neurexin 3β are related genes with related functions. Thus, the present invention also provides methods of diagnosing or predicting susceptibility to autism or an autism related disorder such as autism spectrum disorder by determining the presence or absence of a neurexin-2β or neurexin 3β gene variant. If neurexin 2β or neurexin 3β contributes up to 2.2% or less to autism in a particular population, the power to detect at least a single change is 0.8 or less. Thus, larger sample sizes are needed to detect single base variants. Additionally, neurexin 2β or neurexin 3β may be more common than neurexin 1 in some populations.

The methods of the invention can be used to quickly, easily and reliably diagnose or predict susceptibility to autism. The methods of the invention can also be advantageous in that they can be useful for predicting those individuals who are at increased risk of producing offspring having autism or at increased risk of developing autism. The methods of the invention are also advantageous in that they can be useful for predicting individuals who may benefit from prophylactic treatment for autism.

In one aspect, the invention provides an isolated nucleic acid molecule which encodes a variant allele of a human neurexin 1 or 1β gene. A variant allele of a human neurexin 1β gene is a nucleotide sequence of a neurexin-1β gene containing one or more changes as compared to the wild-type neurexin-1β gene or an amino acid sequence of a neurexin-1β polypeptide containing one or more change as compared to the wild-type neurexin-1β polypeptide sequence. The sequence of the human neurexin 1β gene can be found in GenBank as accession number NM_138735 [SEQ ID NO:1]. Furthermore, the sequence of neurexin 1β from other species can be found in the GenBank database (Genbank accession numbers AAL40261 and AAA19906). A variant allele of a human neurexin 1 gene is a nucleotide sequence of a neurexin-1 gene containing one or more changes in any one of the exons of the neurexin-1 gene as compared to the wild-type neurexin-1 gene or an amino acid sequence of a neurexin-1 polypeptide containing one or more change(s) as compared to the wild-type neurexin-1 polypeptide sequence. For example, a variant allele of a human neurexin 1 gene can include a nucleotide sequence change in any one of the exons of the neurexin 1 gene. Particularly, a variant allele includes a nucleotide base pair change in exon 1, 7, 9, 10 and/or 13 of the neurexin 1 gene as compared to the wild-type neurexin 1 gene sequence.

In one aspect, a neurexin-1β variant is located in exon 1 of the human neurexin-1 gene. For example, p.S14L (c.41C>T); [SEQ ID NO:4] or p.T40S (c.118A>T); [SEQ ID NO:6] is located within exon 1 as shown in FIG. 1 [SEQ ID NO:1]. As used herein, the term "p.S14L" or "c.41C>T" means a single nucleotide polymorphism (cytosine to thymidine substitution) at nucleotide 41 within exon 1 in the neurexin-1β gene; which occurs within a triplet encoding amino acid 14 of the neurexin-1β polypeptide. The term "p.T40S" or "c.118A>T" means a single nucleotide polymorphism (adenosine to thymidine substitution) at nucleotide 118 within exon 1 of the neurexin-1β gene; which occurs within a triplet encoding amino acid 40 of the neurexin-1 polypeptide. The polymorphism within the p.S14L [SEQ ID NO:4]; (c.41C>T); [SEQ ID NO: 3] and p.T40S [SEQ ID NO:5]; (c.118A>T) [SEQ ID NO:6] alleles results in structural missense mutations.

Alternatively, a variant neurexin-1β allele may contain a mutation such that a single nucleotide polymorphism occurs at a location other than that described for p.S14L (c.41C>T) or p.T40S (c.118A>T). A variant neurexin-1β allele may also have more than a single point mutation. For example, a neurexin-1β gene having both p.S14L (c.41C>T) and p.T40S (c.118A>T) mutations are included and are useful as markers for methods for diagnosing or predicting susceptibility to autism and autism related disorders in an individual.

In another aspect, a variant of the present invention may be located in any one of the 24 exons of the neurexin 1 gene. For example, a variant may be located at exon 1, exon 7, exon 9, exon 10 or exon 13 of the human neurexin-1 gene. Such variants include, for example, nucleotide base changes located at nucleotide 215, 229, 275, 350, 941, IVS4+1, 408-409, 490064, 490213, 530859, 489930, 490106, 490208, 497082, or any other nucleotide within the neurexin-1 gene. Preferable variants include c.215G>C, c.229C>T, c.275G>C, c.350A>C, c.941T>A, IVS4+1G>A, c.408-409C>T, c.490064C>T, c.490213G>A, c.530859C>A, c.489930A>T, c.490106C>T, c.490208A>G, c.497082G>T. As used herein, the term "c.XC>T" means a single nucleotide polymorphism (cytosine to thymidine substitution) at base pair position "X" wherein X corresponds to the numeric position of the nucleotide. As used herein, the term "c.XG>C" means a single nucleotide polymorphism (guanine to cytosine substitution) at base pair position "X" wherein X corresponds to the numeric position of the nucleotide. As used herein, the term "c.XA>C" means a single nucleotide polymorphism (adenine to thymidine substitution) at base pair position "X" wherein X corresponds to the numeric position of the nucleotide. As used herein, the term "c.XT>A" means a single nucleotide polymorphism (thymidine to adenine substitution) at base pair position "X" wherein X corresponds to the numeric position of the nucleotide. As used herein, the term "c.XG>A" means a single nucleotide polymorphism (guanine to adenine substitution) at base pair position "X" wherein X corresponds to the numeric position of the nucleotide. As used herein, the term "c.XC>A" means a single nucleotide polymorphism (cytosine to adenine substitution) at base pair position "X" wherein X corresponds to the numeric position of the nucleotide. As used herein, the term "c.XA>T" means a single nucleotide polymorphism (adenine to thymidine substitution) at base pair position "X" wherein X corresponds to the numeric position of the nucleotide. As used herein, the term "c.XA>G" means a single nucleotide polymorphism (adenine to guanine substitution) at base pair position "X" wherein X corresponds to the numeric position of the nucleotide. As used herein, the term "c.XG>T" means a single nucleotide polymorphism (guanine to thymidine substitution) at base pair position "X" wherein X corresponds to the numeric position of the nucleotide.

The term "arg8pro" means a change in amino acid at position 8 of the neurexin 1 polypeptide from arginine to proline. The term "leu13phe" means a change in amino acid position 13 from the wild type leucine to phenylalanine. The term "gly28ala" refers to a change in amino acid position 28 from glycine to alanine. The term "glu53ala" refers to a change at amino acid position 53 from glutamine to Alanine. The term "phe250tyr" refers to a change at amino acid position 250 from phenylalanine to tyrosine. The term "pro429ser" refers to a change at amino acid position 429 from proline to serine. The term "thr665ile" refers to a change at amino acid position 665 from threonine to Isoleucine. The term "glu715lys" refers to a change at amino acid position 715 from glutamine to lysine. The term "leu869met" refers to a change at amino acid position 869 from leucine to methionine. The term "glu620asp" refers to a change at amino acid position 620 from glutamine to asparagine. The term "pro679leu" refers to a change at amino acid position 679 from proline to leucine. The term "glu713gly" refers to a change at amino acid position 713 from glutamine to Glycine. The term "glu730his" refers to a change at amino acid position 730 from glutamine to histidine. Additional nomenclature corresponding to the variants is indicated in Table 4.

Alternatively, a variant neurexin-1 allele may contain a mutation such that a single nucleotide polymorphism occurs at a location other than that described above. A variant neurexin-1 allele may also have more than a single point mutation.

The invention provides methods for determining a subject's susceptibility to autism or an autism spectrum disorder. Accordingly, in certain embodiments, the variant alleles as set forth in Table 3 and 4 may be used to identify an individual having autism or to determine whether an individual is predisposed to autism or an autism related or autism spectrum disorder. The autism spectrum disorder may be selected from the group consisting of autism, Asperger's disorder and Pervasive Development Delay (PDD). A variant allele of the neurexin-1β gene is also useful to assay drugs and agents for use in treating autism or an autism related disorder.

The presence of a p.S14L (c.41C>T) or p.T40S (c.118A>T) variant and other neurexin 1 or neurexin-1β variants can be conveniently detected for example, by allelic discrimination assays or sequence analysis. Primers specific for the p.S14L (c.41C>T) or p.T40S (c.118A>T) variants can be found in Example 1. (See Table 2) [SEQ ID NOS:7-22].

A neurexin variant also can be located in a non-coding region of the neurexin-1b locus. Non-coding regions include, for example, intron sequences as well as 5' and 3' untranslated sequences. As used herein, the term "neurexin variant" is intended to include variants of the wild-type human neurexin 1 gene. The term "neurexin variant" is also intended to include variants of the wild-type human neurexin-β gene such as human neurexin-1β, -2β, or -3β.

A variety of means can be useful for determining the presence or absence of a neurexin variant. Since a neurexin variant may be a nucleotide sequence of a neurexin gene containing one or more changes as compared to the wild-type neurexin gene or an amino acid sequence of a neurexin polypeptide containing one or more changes as compared to the wild-type neurexin polypeptide sequence, genetic, serological and other biochemical methods can be useful. For example, enzymatic amplification of nucleic acid from a subject can be used to obtain nucleic acid for subsequent genetic analysis. The presence or absence of a neurexin variant can also be determined directly from the individual's nucleic acid without enzymatic amplification. Analysis of nucleic acid from an individual, whether amplified or non-amplified, can be performed using a variety of techniques such as, polymerase chain reaction (PCR) based analysis, ligase chain reaction (LCR) based analysis, sequence analysis, and/or other electrophoresis analysis. Such techniques can be used alone or in combination and/or in combination with other allelic detection methods.

Single nucleotide polymorphisms (SNPs) are DNA sequence variations that occur when a single nucleotide (A, T, C, or G) in the genome sequence is changed from the native or wild-type sequence. There are many techniques for SNP detection and genotyping, including without limitation, restriction fragment length polymorphism PCR (RFLP-PCR), single-stranded conformation polymorphisms (SSCP) [Hayashi Methods Applic. 1:34-38 (1991)], allele specific hybridization [Bao et al., Nucleic Acids Res. 2005; 33(2): e15.], heteroduplex mobility assay [Delwart et al., Science 262:1257-1261 (1993); White et al., Genomics 12:301-306 (1992)], primer extension, allele specific oligonucleotide ligation [Black et al., J Med Entomol. 2006 March; 43(2): 238-47], sequencing [Sears et al., Biotechniques 13:626-633 (1992); Zimmerman et al., Methods Mol. Cell Biol. 3:39-42 (1992); Fu et al., Nature Biotech. 16:381-384 (1998); Chee et al., Science 274:610-614 (1996); Drmanac et al., Science 260:1649-1652 (1993)], RNA mismatch analysis (Winter et al., PNAS 82:7575-7579 (1985)].

The presence or absence of a neurexin-β variant can entail amplification of an individual's nucleic acid using PCR. The nucleic acid to be amplified can be single- or double-stranded DNA or RNA molecule, including, for example, genomic DNA, cDNA and mRNA. Use of PCR for amplification of nucleic acid is well known in the art (see, for example, Erlich HA et al 1991 Science Vol 252 (5041): 1643-1651. Such analysis can be performed, if desired, using single nucleotide based polymorphism analysis such as in a Taqman. SNP assay (available from Applied Biosystems, Foster City, Calif.).

Any of a variety of different primers can be used to amplify an individual's nucleic acid by PCR or LCR to identify a neurexin 1 or neurexin-β variant such as a neurexin 1β, 2β or 3β variant. For example, the PCR primers listed in Example 1 (SEQ ID NOS: 7 and 8; (NX1-1D, NX1-1U)) can be used to amplify specific regions of the neurexin-1β locus. As non-limiting examples, the region surrounding p.S14L [SEQ ID NO:4] can be amplified using SEQ ID NO: 7 and 8; p.T40S [SEQ ID NO:6] can also be amplified using SEQ ID NOS: 7 and 8 (NX1-1D, NX1-1U). As understood by one skilled in the art, additional primers for amplification can be designed based on the sequence flanking the neurexin-1β region of interest.

Sequence analysis also is useful for determining the presence or absence of a neurexin-1 or neurexin-β variant. A neurexin-1β variant can be detected by sequence analysis using primers disclosed herein, for example, the PCR primers [SEQ ID NOS: 7-22] listed in Example 1 (Table 2). As understood by one skilled in the art, additional primers for sequence analysis can be designed based on the sequence flanking the neurexin-1β region of interest. As a non-limiting example, a sequence primer can contain about 15 to 30 nucleotides of a sequence up to about 600 base pairs upstream or downstream of the region of interest.

Electrophoresis analysis can also be used in the methods of the invention. These include without limitation, analysis using slab gel electrophoresis or capillary electrophoresis. Such methods of electrophoresis analysis are known in the art as described, for example, in Ausubel et al., Current Protocols in Molecular Biology, John Wiley & Sons ISBN: 0-471-50338-X copyright 2000-2006.

Restriction fragment length polymorphism (RFLP) analysis can also be used for determining the presence or absence of a neurexin-1β variant. Such methods are known in the art and described, for example, in Jarcho et al., in Dracopoli et al., Current Protocols in Human Genetics, John Wiley & Sons, New York; Innis et al., (Ed.), PCR Protocols, San Diego: Academic Press, Inc. (1990); and Online Tools SNP Analysis Protocols available at URL address: http://bioinfo.bsd.uchicago.edu/SNP_cutter.htm).

Genetic methods for determining the presence or absence of a neurexin-1β variant include use of a biological sample obtained from a subject from which nucleic acid can be prepared. This includes, for example, blood, saliva, cheek swab, chorionic villus, embryonic or fetal cells, germ cells, cord blood cells, amniotic fluid, or other bodily fluid or tissue that contains nucleic acid.

Antibody based methods also can be used for determining presence or absence of a neurexin-1 or neurexin-β variant. For example, an antibody that is specifically reactive with a neurexin-1 or neurexin-1β, 2β or 3β variant polypeptide or fragment thereof can be used to detect the presence or absence of the variant in an individual or biological sample.

Current methods for diagnosing autism are based on observation of the individual's communication, behavior and developmental levels. Many other developmental or behavioral disorders share overlapping systems such as odd or eccentric behavior or problems with hearing. In addition, some overlapping symptoms co-occur with autism. In order to provide effective treatment, it is important to distinguish autism from other conditions. Early and accurate diagnosis of autism is key to providing an appropriate and effective treatment plan. The present invention is particularly valuable as it allows for an earlier and potentially more accurate method for diagnosing autism. Additionally, as there are no currently available medical tests for diagnosing autism, use of the present invention along with observational and behavioral methods of diagnosis provides a particularly effective and complementary diagnosis of autism or autism related disorder.

Thus, the invention provides for a diagnostic method for determining the onset or the presence of autism spectrum disorder in an individual by detecting the existence of a change in a neurexin-β gene. The invention further provides a diagnostic method for determining the onset or the presence of autism spectrum disorder in an individual by detecting the existence of a change in a segment of the neurexin 1β gene located within the portion of exon 1 as set forth in SEQ ID NO:3 and SEQ ID NO:5. (FIGS. 2 and 3). In one aspect, the segment comprises the human neurexin-1β gene and is located in exon 1 at amino acids position 1_to_86_(GenBank accession number NM_138735 [SEQ ID NO:1]). The invention also provides for a diagnostic method comprising detecting the existence of a change in amino acid at positions 14 and 40 [FIG. 1].

As used in the context of the present invention, autism includes any form of autism known as autism or an autism related disorder such as autism spectrum disorder. Also included are Asperger's Syndrome and Pervasive Developmental Disorder (PDD) [0018]. The American Psychiatric Association Diagnostic and Statistical Manual ("DSM-IV"), Fourth Edition (2000) provides current diagnostic criteria for autistic disorder and is provided at URL address http://www.behavenet.com/capsules/disorders/autistic.htm, which is hereby incorporated by reference in its entirety.

The invention also provides for a diagnostic method for determining that an individual has a genetic abnormality that predisposes the individual and/or his or her offspring to autism or autism spectrum disorder. Thus, the present invention also relates to a genetic testing method for predicting susceptibility or increased risk of developing autism or autism spectrum disorder in an offspring. The method comprises detecting in a biological sample from an individual (e.g. buccal cells, blood cells, germ cell, chorionic villus tissue, etc.) the existence of a mutation in exon 1 of the neurexin-1β gene. For example, an individual identified as having a neurexin-1β allelic variant having an amino acid sequence variant in the exon 1 region, such as a p.S14L (c.41C>T) and/or p.T40S (c.118A>T) mutation, indicates that the individual is at increased risk of having offspring who will develop autism or an autism related disorder.

A diagnostic method includes detecting in a biological sample such as in tissue or cells from an individual, the presence or absence of a gene or gene product. Such a gene or gene product can correspond to (c.41C>T) [SEQ ID NO. 3], (c.118A>T) [SEQ ID NO. 5], a protein encoded by SEQ ID NO. 3 or SEQ ID NO. 5, a nucleic acid comprising a sequence hybridizable to SEQ ID NO:1, SEQ ID NO:3, or SEQ ID NO:5, or a complement of SEQ ID NO:1, SEQ ID NO:3, or SEQ ID NO:5 under conditions of high stringency, or a protein comprising a sequence encoded by the hybridizable sequence, a nucleic acid at least 80% homologous, or at least 85% homologous, or preferably at least 90% homologous to any one of SEQ ID NOS: 1, 3 or 5, or a complement of SEQ ID NO:1, SEQ ID NO:3, or SEQ ID NO:5 as determined using the NBLAST algorithm, or a transcript or protein encoded thereby.

The individual diagnosed by a method of the present invention may not be known to be autistic (i.e. may not exhibit any autistic symptoms or behaviors). However, if the individual has the genetic abnormality such as, the individual is heterozygous or homozygous for p.S14L (c.41C>T) and/or p.T40S (c.118A>T) mutation, then this diagnosis signifies that the individual may have autism or an autism spectrum disorder and/or the individual could bear children who are predisposed to developing autism. It is sufficient that the genetic abnormality or mutation occur in one chromosome of the person (e.g. the person can be a heterozygous carrier of p.S14L (c.41C>T) and/or p.T40S (c.118A>T) allele(s)).

In another aspect, the method of the invention involves detecting changes in the neurexin-1β gene such as exon 1 of the neurexin-1β gene. A neurexin-1β gene is a gene that encodes a neurexin protein. The present invention is not limited to any particular mechanism or method by which a variant neurexin-1β allele may produce symptoms of, or susceptibility to, autism. Thus, the invention includes other changes (e.g. mutations) and differences in sequence of the neurexin-1β gene from the wild-type gene. The size or extent of the change may involve addition, substitution or deletion of one or more nucleotide in the DNA sequence resulting in a polymorphic allele or resulting in the deletion, addition, or substitution of at least one amino acid in the neurexin protein.

A diagnostic method of the present invention includes comparing the amount of one or more of the above-indicated gene or gene product present in a subject with a normal biological sample (e.g. tissue sample from non-autistic individual) or a predetermined standard for a normal biological sample, where a difference (e.g. elevated or decreased) amount of the gene product in the subject as compared to the normal sample indicates a risk of developing autism or autism spectrum disorder or the onset or progression of autism or autism spectrum disorder in the subject.

In another aspect, the invention provides a method for determining the level of severity or prognosis of an individual for autism or an autism spectrum disorder by measuring the presence or absence or difference in amount of a neurexin-1β gene or gene product (e.g. p.S14L (c.41C>T) and/or T40S (c.118A>T) allele or protein in a sample derived from the individual wherein the gene or gene product is a DNA corresponding to SEQ ID NO: 3 or nucleic acid derived therefrom, SEQ ID NO: 5 or nucleic acid derived therefrom, a protein encoded by SEQ ID NO:3 or SEQ ID NO:5, a nucleic acid comprising a sequence hybridizable to SEQ ID NO:3 or SEQ ID NO:5 under conditions of high stringency, or a protein comprising a sequence encoded by the hybridizable sequence, a nucleic acid at least 80% homologous, or at least 85% homologous, or preferably at least 90% homologous to SEQ ID NO:1, SEQ ID NO:3 or SEQ ID NO:5 or a complement thereof, as determined using the NBLAST algorithm, or a protein or transcript encoded thereby.

A comparison of the amount of the gene product in a test subject is made to the amount of gene product present in a non-autistic or normal biological sample or predetermined standard for a negative control.

The invention also provides for a diagnostic kit comprising a set of primers or a nucleic acid probe specific for part or all of a region of the gene encoding p.S14L (c.41C>T) or p.T40S (c.118A>T) or neurexin-1β gene segment identified by the present invention as diagnostic of autism or autism spectrum disorder. Such probes include, for example, PCR primers that can be used to amplify a p.S14L (c.41C>T) and/or p.T40S (c.118A>T) allele. In other kits, the probe may be a protein based probe comprising an antibody specific for the diagnostic segment of neurexin-1β, 2β or 3β.

Thus, in another aspect, the invention includes antibodies recognizing and binding to the amino acid sequence corresponding to SEQ ID NO:1, SEQ ID NO:3 or SEQ ID NO:5. Antibodies which recognize and bind to the amino acid variants as listed in Table 4 are also included. Such antibodies can be polyclonal, monoclonal, single chain, chimeric, humanized, fully human or any other type of antibody or fragment thereof useful for diagnostic or therapeutic purposes of the present invention.

The invention also provides for a method of treating an individual predisposed to autism or diagnosed as having autism or autism spectrum disorder by gene therapy based on the p.S14L (c.41C>T) or p.T40S (c.118A>T) gene or gene product. For example, an individual or the offspring of an individual diagnosed as having a neurexin-1β, 2β or 3β allelic variant or mutation, can be therapeutically or prophylactically treated by administering DNA molecules encoding the appropriate wild-type neurexin-β allele. Alternatively, the administered DNA molecules can comprise DNA or RNA sequences able to hybridize to the variant or mutant sequence thereby reducing or eliminating expression of the variant or mutant neurexin protein.

The terms used herein have the meanings recognized and known to those of skill in the art. However, for convenience, particular terms and their meanings are set forth below.

"Treatment" refers to the administration of medicine or the performance of medical procedures with respect to a patient, for either prevention (prophylactic) or therapeutic, or to alleviate or cure the illness or one or more disorder associated with the illness or disorder.

A "therapeutically effective amount" is an amount sufficient to decrease, change or prevent one or more symptom associated with autism associated with the presence of at least one of the neurexin-1β, 2β or 3β variants identified in the present invention.

A "variant" is one or more polynucleotide or polypeptide that differs in sequence or is polymorphic from a reference polynucleotide or polypeptide. For example, a polynucleotide having a sequence that differs from a wild-type neurexin-1, 2β or 3β gene is a variant allele.

"Detecting a target nucleic acid sequence" refers to determining the presence of a particular nucleic acid sequence in a sample or determining the amount of a particular nucleic acid sequence in a sample as an indication of the presence of the target nucleic acid sequence.

"Amplifying" refers to the generation of additional copies of a nucleic acid sequence. A variety of methods are known in the art and are useful to amplify nucleic acid sequences. Including the polymerase chain reaction (PCR), ligase chain reaction (LCR). Alternatively, the term "amplifying" as used herein, also refers to the detection of a particular target nucleic acid sequence using methods having increased sensitivity and ability to reveal the presence of a target nucleic acid sequence. For example, the presence of a particular target nucleic acid sequence may be "amplified" by use of radioactive hybridization probe able to bind to the target sequence and thereby signal or indicate presence of the target sequence in a sample.

A "signal sequence" is a region of nucleotide sequence of a gene occurring at the beginning of the coding sequence of a protein and which directs the protein to a particular site or compartment in the cell such as the surface of a cell. This sequence encodes a signal peptide which is N-terminal to the mature polypeptide and which directs the host cell to translocate the polypeptide.

A "marker" means a serological, genetic or other biochemical factor, the presence of which correlates with a clinical or behavioral indicator diagnostic of autism or an autism related disorder.

It is understood that the present invention is not to be limited in scope by specific examples described herein. Various modifications of the invention in addition to those described herein will become apparent to those skilled in the art from the foregoing description and are intended to fall within the scope of the invention.

EXAMPLE 1

Subjects and Methods

The study was approved by the Institutional Review Board. The South Carolina autism project (SCAP) enrolled ethnically diverse families from South Carolina. The SCAP population has been described in detail [12] (Table 1). All patients have had a clinical genetic examination, and all meet the DSM IV-R criteria for autism. All patients were initially classified as having autism based on the childhood autism rating scale [13]. In addition, the autism diagnostic interview-revised [ADI-R, [14]] was administered for 175 patients, 167 of whom (139 males, 28 females) met the criteria for autism by this instrument. The Vineland Adaptive Behavior Scale [VABS; [15]] was administered to every patient as part of the SCAP. Cognitive testing was performed through the individual child's school system or the South Carolina Department of Disabilities and Special Needs, using standardized tests chosen according to the individual child's level of verbal ability [12; 16].

TABLE 1

Gender and ethnicity of austim patients and controls

| | Caucasian | | Afro-American | | |
| --- | --- | --- | --- | --- | --- |
| | Male | Female | Male | Female | Total |
| Patients Scanned[a] | | | | | |
| South Carolina | 48 | | | | 48 |
| Midwest | 21 | 3 | | | 24 |
| Total Exon 1 sequenced[b] | 69 | 3 | | | 72 |
| South Carolina | 45 | 22 | 45 | 7 | 119 |
| Midwest | 52 | 12 | 8 | 1 | 73 |
| Total Controls Exon 1 sequenced[b] | 97 | 34 | 53 | 8 | 192 |
| South Carolina | | 335 | | 194 | |
| Midwest | | 200 | | | |
| Total | | 535 | | 194 | 729 |

Note:
[a]Patients were scanned for mutations in the neurexin 1β, 2β, and 3β genes
[b]Exon 1 of the neurexin 1β gene was sequenced The autism patients from Midwest were previously described [17] (Table 1). The inclusion criteria were [17]: (1) diagnosis of autistic disorder, by use of the Autism Diagnostic Interview. Revised (ADI-R) [14] and age-appropriate versions of the Autism Diagnostic Observation Schedule [18] or the Pre-Linguistic Autism Diagnostic Observation Schedule [19]; (2) mental age>18 mo, as assessed by the Vineland Adaptive Behavior Scales (Sparrow et al. 1984); (3) nonverbal IQ>35; (4) confirmation of the diagnosis of autistic disorder, by a child psychologist; and (5) exclusion of known etiologies of autistic disorder, by physical examination, including neurological examination and Wood's lamp examination to exclude tuberous sclerosis [20].

The three β-neurexin genes were scanned with DOVAM-S, a robotically enhanced, high throughput, and multiplex form of SSCP: half a megabase of genomic sequence is analyzed on one gel under five generic conditions [21]. 391 unique mutations (525 total mutations) in six genes were detected in blinded analyses [22]. To detect NRXN mutations, genomic DNA and standard PCR conditions [23] were used to generate separate PCR segments labeled with [α33P] dATP (Amersham, Boston, Mass.) which included all coding exons and splice junctions of the NRXN genes. Sequences of the primers are in Table 2. PCR amplification was performed using 1 unit of TaqGold DNA polymerase, in a total volume of 25μ 50 mM KCl, 10 mM Tris-HCl, (pH 8.3), 2.5 mM $MgCl_2$, 200 μM of each dNTP, for 35 cycles (15 seconds at 94° C., 30 seconds at 60° C. and 1 minute at 72° C.), after a 10-minute initial period of DNA denaturation and enzyme activation at 94° C. The segments were amplified and pooled by the ABI PRISM 877 integrated thermal cycler (Applied Biosystem, Inc., Foster City, Calif.), denatured, and electrophoresed under five non-denaturing conditions in which gel matrix, buffer, temperature, and additive were varied as previously described [23].

TABLE 2

NRXN1 Primers

| SEQ ID NO. | Exon | Name | Sequence (5'-3') | bp | $T_m$ | Position | Amplicon Size |
| --- | --- | --- | --- | --- | --- | --- | --- |
| 7 | 1 | NX1-1d | gcgcccaaactttgcct | 18 | 58 | 681465 | 365 |
| 8 | | NX1-1u | tagaaagaggggagcgagg | 19 | 60 | 681829 | |
| 9 | 2 | NX1-2d | cttgctaatgtgcagacttga | 21 | 60 | 791437 | 331 |
| 10 | | NX1-2u | aaggaagcatccaagaagca | 20 | 58 | 791767 | |
| 11 | 3 | NX1-3d | aatggtgactagtcaacttaat | 22 | 58 | 936920 | 301 |
| 12 | | NX1-3u | aacggatgcaaaacagtgct | 20 | 58 | 937220 | |
| 13 | 4 | NX1-4d1 | tcatccattgtagatatagagt | 22 | 58 | 974811 | 290 |
| 14 | | NX1-4u1 | attgcatggcagtggctgtt | 20 | 60 | 975010 | |
| 15 | 4 | NX1-4d2 | ggaaatgtgagactggttgg | 20 | 60 | 975031 | 222 |
| 16 | | NX1-4u2 | gcccactatcataaataatatag | 23 | 60 | 975252 | |
| 17 | 5 | NX1-5d | tgagagaatctgttaggacc | 20 | 58 | 1084619 | 212 |
| 18 | | NX1-5u | ctaaggaatataacatgcaaca | 22 | 58 | 1084830 | |
| 19 | 6 | NX1-6d1 | ttcagtgaactcaatgatcac | 21 | 58 | 1106163 | 239 |
| 20 | | NX1-6u1 | ctctcgtccacatggtatga | 20 | 60 | 1106401 | |
| 21 | 6 | NX1-6d2 | tcctctatgccatgtacaag | 20 | 58 | 1106341 | 311 |
| 21 | | NX1-6u2 | ttccttcctgattgcattcc | 20 | 58 | 1106651 | |

Results and Discussion

A total of 3.2 Megabases of genomic sequence (the regions of likely functional significance) of three β-neurexin genes were initially scanned in 72 patients with autism (48 South Carolina Caucasians and 24 Midwest US Caucasians, 69 males and 3 females) and 48 Caucasian controls without autism, followed by sequencing of exon 1 of neurexin 1β in 131 additional Caucasian and 61 Afro-American patients with autism from South Carolina and the Midwest. Two missense variants (c.41C>T [SEQ ID NO:4], p.S14L [SEQ ID NO:4], and c.118A>T [SEQ ID NO:5], p.T40S [SEQ ID NO:6]) were identified in the neurexin 1β gene in four South Carolina Caucasian patients (Table 3). An in-frame deletion of five GGC triplets and two different in-frame insertions (a single GGC triplet and a two GGC triplet repeats) were identified in the neurexin 1β gene in a total of nine patients (Table 3). No structural variants were found in the neurexin 2β gene and the neurexin 3β gene.

and good social skills. However, she reported she stammered as a child. There is a paternal history of learning disabilities.

Patient #15107 has autism by ADI-R criteria. He has a seizure disorder, mild dysmorphic facial features and hypopigmented lesions of the skin at various locations. His IQ was 68. The p.S14L [SEQ ID NO:4]; (c.41C>T) [SEQ ID NO:3] missense mutation is also present in one brother who has learning disorder and hyperactivity. Another brother, who does not carry this variant, is in law school. He displays some hyperactivity. The father who carries the p.S14L [SEQ ID NO:4]; (c.41C>T) [SEQ ID NO:3] missense mutation is hyperactive. The mother of patient 15107 does not carry the p.S14L [SEQ ID NO:4]; (c.41C>T) [SEQ ID NO:3] variant and is normal but there is a history of mental retardation on her side.

Patient #13296 who is heterozygous for the p.T40S [SEQ ID NO:6]; (c.118A>T) [SEQ ID NO:5], missense variant, has autism as determined by ADI-R criteria. His IQ is 58 and he

TABLE 3

Structural variants identified in the Neurexin-1β gene in patients with autism

| No. | Patient ID | Gender | Ethnicity | Exon | NT change | AA change | Family members |
|---|---|---|---|---|---|---|---|
| 1 | 8139 | male | Caucasian | 1 | c.41 C > T | p.S14L | mother wt, father +/−, sister +/− |
|   | 15107 | male | Caucasian | 1 | c.41 C > T | p.S14L | mother wt, father +/−, brother 1 +/−, brother 2 +/− |
|   | 17160 | female | Caucasian | 1 | c.41 C > T | p.S14L | n/a |
| 2 | 13296 | male | Caucasian | 1 | c.118 A > T | p.T40S | father wt, mother +/−, sister +/− |
| 3 | 1653 | male | Caucasian | 1 | c.78 ins GGC | p.26 ins G |   |
|   | 13302 | female | Afro-American | 1 | c.78 ins GGC | p.26 ins G |   |
| 4 | 2154 | female | Caucasian | 1 | c.78 ins GGCGGC | p.26 ins GG |   |
| 5 | Common[a] |   |   | 1 | c.50 G > T | p.G17V |   |
| 6 | Common[b] |   |   | 1 | c.64-78 del 5 GGC | p.22-26 del 5G |   |

[a] more than 24 patients
[b] six African-American patients

Case-Control Analysis

Sequencing of exon 1 of neurexin 1β in 535 healthy Caucasian controls from the Midwest, South Carolina and 194 healthy Afro-American controls from South Carolina did not reveal these two missense variants or any other missense changes (4/264 vs. 0/729, P=0.0049; Caucasian 4/203 vs. 0/535, P=0.0056 Fisher exact test).

The in-frame insertion of a single GGC triplet repeat in neurexin 1β was identified in three controls (2/264 vs. 3/729, p=0.40). The in-frame deletion of a five GGC triplet repeats was found in Afro-American patients and controls only (6/61 vs. 11/194, P=0.19, Fisher exact test), indicating this variant is a common polymorphism in Afro-Americans. No in-frame insertion of the two GGC triplet repeats in neurexin 1β was identified in 535 healthy Caucasian controls and 194 healthy Afro-American controls (1/264 vs. 0/729, p=0.27).

NRXN 1β Family Studies

Table 3 summarizes the structural variants identified in the Neurexin-1β Patient #8139 met ADI-R criteria for autism. He is heterozygous for the p.S14L [SEQ ID NO:4]; (c.41C>T) [SEQ ID NO:3], missense mutation as is his sister. He has an IQ of 50, suffers from seizures, and has some mild facial dysmorphism and hypopigmented areas on his body. The sister has an IQ of 123, a central auditory processing problem, and decreased social interaction, but she does meet criteria for Asperger syndrome. The father of patient 8139 is heterozygous for the p.S14L [SEQ ID NO:4]; (c.41C>T) [SEQ ID NO:3], missense mutation, and is good at math. The mother who does not have the p.S14L [SEQ ID NO:4]; (c.41C>T) [SEQ ID NO:3] change, has above average cognitive function has a flat midface. He has a sister who also carries the p.T40S [SEQ ID NO:6]; (c.118A>T) [SEQ ID NO:5] missense mutation. The sister is not reported to have any behavior or learning problems. The mother, who is heterozygous for the p.T40S [SEQ ID NO:6]; (c.118A>T) [SEQ ID NO:5] variation, had learning problems and experienced periods of depression. Additionally, she has a family history of learning problems as does the father of patient 13296, who does not carry the p.T40S [SEQ ID NO:6]; (c.118A>T) [SEQ ID NO:5] variant.

Two missense variants were identified in exon 1, in which the N terminus of all three β-neurexins contains an unusual cleaved signal sequence [Ushkaryov et al., 1994]. The signal sequences of the β-neurexins are not homologous to each other, but they share several characteristics. They are unusually long (46 amino acids for neurexins 1β and 2β, 35 for neurexin 3β), quite hydrophobic, contain high concentrations of short chain amino acids and don't have the characteristics of a cleaved signal sequence [Hortsch and Meyer, 1986; von Heijne, 1986]. The unusual structures of the signal sequences of the β-neurexins raise the possibility that there may be more mechanistic heterogeneity in signal sequence function than currently appreciated. Thus, mutations in this region may affect the signaling function.

i) Family data originates from written records from telephone conversations or brief interviews; ii) Incomplete penetrance in neuropsychiatric disease is generally expected from lack of concordance in monozygotic twins, but it is also possible that the lack of penetrance may arise from partial equilibrium with a linked causative mutation; iii) In 6 out of 1,000 case control analyses, a p value of equal or greater than this magnitude would be expected by chance; iv) The patients with autism were non-Hispanic Caucasians of European origin, but detailed ethnicity data are not available, so population stratification cannot be excluded. However, 335 of the controls were ascertained in the same South Carolina population; sequencing of exon 1 of the neurexin-1 gene did not reveal ether p.S14L [SEQ ID NO:4]; (c.41C>T) [SEQ ID NO:3], or the p.T40S [SEQ ID NO:6]; (c.118A>T) [SEQ ID NO:5], or any novel missense structural variant.

Therefore, neurexin-1β missense variants are associated with autism in a case-control study (p<0.006). This finding and the binding of neurexin to NLGN indicate a causative link with autism. Studies indicate that early diagnosis of autism or autism related disorders may be associated with dramatically improved outcomes.

EXAMPLE 2

The neurexin 1 gene consist of 24 exons. Neurexin 1 alpha is composed of exons 1 thru 24. Neurexin 1 beta is a carboxy terminal segment of neurexin alpha. It contains exons 18 thru 24 plus an alternatively spliced exon located in intron 17 of the neurexin alpha gene. Variants located within any of these exons may be associated with autism and indicate a causative link with autism. The neurexin alpha/beta gene was analyzed by staining or sequencing in an additional sample of patients. A total of 190 cases or 192 controls were analyzed. In total, there were 14 patients with cohort specific structural variants and 3 controls with cohort specific structural variants (p<0.009, see Table 4).

TABLE 4

Neurexin 1 Structural Variants

| | NT# | wt base | mut base | AA change | Exon # |
|---|---|---|---|---|---|
| Patient ID# | | | | | |
| 15057 | 215 | G | C | arg8pro (p.R8P) | 1 |
| 14630 | 229 | C | T | leu13phe (p.L13F) | 1 |
| 17160 | 275 | G | C | gly28ala (p.G28A) | 1 |
| 2296 | 350 | A | C | glu53ala (p.E53A) | 1 |
| 1653 | 941 | T | A | phe250tyr (p.F250Y) | 1 |
| 9567a | IVS 4 + 1 | G | A | | |
| 1738 | 408409 | C | T | pro429ser (p.P429S) | 7 |
| 13104 | 490064 | C | T | thr665ile (p.T665I) | 9 |
| 17335 | 490213 | G | A | glu715lys (p.E715L) | 9 |
| 1738 | 530859 | C | A | leu869met (p.L869M) | 13 |
| Controls | | | | | |
| CMS9385 | 489930 | A | T | glu620asp (p.E620D) | 9 |
| MC232 | 490106 | C | T | pro679leu (p.P679L) | 9 |
| MC206 | 490208 | A | G | glu713gly (p.E713G) | 9 |
| MC232 | 497082 | G | T | glu730his (p.E730H) | 10 |

Therefore, neurexin 1 gene variants were associated with autism in a case-control study (p<0.009). These variants may be used in the early diagnosis of autism or autism related disorders.

REFERENCES CITED

1. Buzin C H, Wen C Y, Nguyen V Q, Nozari G, Mengos A, Li X, Chen J S, Liu Q, Gatti R A, Fujimura F K, Sommer S S. 2000. Scanning by DOVAM-S detects all unique sequence changes in blinded analyses: evidence that the scanning conditions are generic. BioTechniques 28:746-753.
2. Cook E H, Courchesne R Y, Cox N J, Lord C, Gonen D, Guter S J, Lincoln A, Nix K, Haas R, Leventhal B L, Courchesne E. 1998. Linkage-disequilibrium mapping of autistic disorder, with 15q11-13 markers. Am J Hum Genet 62:1077-1083.
3. Dean C, Scholl F G, Choih J, DeMaria S, Berger J, Isacoff E, Scheiffele P. 2003. Neurexin mediates the assembly of presynaptic terminals. Nat Neurosci 6:708-716.
4. Garner C C, Nash J, Huganir R L. 2000. PDZ domains in synapse assembly and signalling. Trends Cell Biol 10:274-280.
5. Hortsch M, Meyer D I. 1986. Transfer of secretory proteins through the membrane of the endoplasmic reticulum. Int Rev Cytol 102:215-242.
6. Ichtchenko K, Hata Y, Nguyen T, Ullrich B, Missler M, Moomaw C, Sudhof T C. 1995. Neuroligin 1: a splice site-specific ligand for beta-neurexins. Cell 81:435-443.
7. Jamain S, Quach H, Betancur C, Rastam M, Colineaux C, Gillberg I C, Soderstrom H, Giros B, Leboyer M, Gillberg C, Bourgeron T. 2003. Mutations of the X-linked genes encoding neuroligins NLGN3 and NLGN4 are associated with autism. Nat Genet 34:27-29.
8. Kleiderlein J J, Nisson P E, Jessee J, Li W B, Becker K G, Derby M L, Ross C A, Margolis R L. 1998. CCG repeats in cDNAs from human brain. Hum Genet 103:666-673.
9. Laumonnier F, Bonnet-Brilhault F, Gomot M, Blanc R, David A, Moizard M P, Raynaud M, Ronce N, Lemonnier E, Calvas P, Laudier B, Chelly J, Fryns J P, Ropers H H, Hamel B C, Andres C, Barthelemy C, Moraine C, Briault S. 2004. X-linked mental retardation and autism are associated with a mutation in the NLGN4 gene, a member of the neuroligin family. Am J Hum Genet 74:552-557.
10. Lobo-Menendez F, Sossey-Alaoui K, Bell J M, Copeland-Yates S A, Plank S M, Sanford S O, Skinner C, Simensen R J, Schroer R J, Michaelis R C. 2003. Absence of MeCP2 mutations in patients from the South Carolina autism project. Am J Med Genet B Neuropsychiatr Genet 117:97-101.
11. Missler M, Sudhof T C. 1998. Neurexins: three genes and 1001 products. Trends Genet 14:20-26.
12. Rowen L, Young J, Birditt B, Kaur A, Madan A, Philipps D L, Qin S, Minx P, Wilson R K, Hood L, Graveley B R. 2002. Analysis of the human neurexin genes: alternative splicing and the generation of protein diversity. Genomics 79:587-597.
13. Schroer R J, Phelan M C, Michaelis R C, Crawford E C, Skinner S A, Cuccaro M, Simensen R J, Bishop J, Skinner C, Fender D, Stevenson R E. 1998. Autism and maternally derived aberrations of chromosome 15q. Am J Med Genet 76:327-336.
14. Tabuchi K, Sudhof T C. 2002. Structure and evolution of neurexin genes: insight into the mechanism of alternative splicing. Genomics 79:849-859.
15. Ullrich B, Ushkaryov Y A, Sudhof T C. 1995. Cartography of neurexins: more than 1000 isoforms generated by alternative splicing and expressed in distinct subsets of neurons. Neuron 14:497-507.
16. Ushkaryov Y A, Hata Y, Ichtchenko K, Moomaw C, Afendis S, Slaughter C A, Sudhof T C. 1994. Conserved domain structure of beta-neurexins. Unusual cleaved signal sequences in receptor-like neuronal cell-surface proteins. J Biol Chem 269:11987-11992.
17. von Heijne G. 1986. A new method for predicting signal sequence cleavage sites. Nucleic Acids Res 14:4683-4690.
18. Yan J, Oliveira G, Coutinho A M, Yang C, Feng J, Katz C, Sram J, Bockholt A, Jones I R, Craddock N, Cook E H J, Vicente A M, Sommer S S. 2004. Analysis of the neuroligin 3 and 4 genes in autism and other neuropsychiatric patients. Molecular Psychiatry.

The invention claimed is:

1. A method for predicting susceptibility to autism in an individual comprising
    detecting the presence of a nucleic acid sequence variant, c.41C>T (SEQ ID NO:3), of a neurexin 1β gene in a biological sample obtained from the individual; and
    predicting that the individual is susceptible to developing autism, wherein autism is an autistic disorder according to DSM-IV criteria.

2. A method for predicting an individual's susceptibility to producing offspring having autism comprising:
    detecting the presence of a nucleic acid sequence variant, c.41C>T (SEQ ID NO:3), of a neurexin 1β gene in a biological sample obtained from the individual; and
    predicting that the individual is susceptible to producing offspring having autism,. wherein autism is an autistic disorder according to DSM-IV criteria.

3. The method of claim 1, wherein the biological sample is selected from the group consisting of blood, saliva, cheek swab, amniotic fluid, cord blood, and placental, chorionic villus, embryonic or germ cells.

4. The method of claim 2, wherein the biological sample is comprised of cells selected from the group consisting of blood, saliva, cheek swab, amniotic fluid, cord blood, and placental, chorionic villus, embryonic or germ cells.

5. The method of claim 1, wherein detection of the nucleic acid sequence variant is accomplished by a method selected from the group consisting of polymerase chain reaction (PCR), ligase chain reaction (LCR), restriction fragment length polymorphism (RFLP), and sequence analysis.

6. The method of claim 2, wherein detection of the nucleic acid sequence variant is accomplished by a method selected from the group consisting of polymerase chain reaction (PCR), ligase chain reaction (LCR), restriction fragment length polymorphism (RFLP), and sequence analysis.

* * * * *

SEQUENCE LISTING

<160> NUMBER OF SEQ ID NOS: 22

<210> SEQ ID NO 1
<211> LENGTH: 180
<212> TYPE: DNA
<213> ORGANISM: Homo sapiens

<400> SEQUENCE: 1

```
atgtaccaga ggatgctccg gtgcggcgcc gagctgggct cgcccggggg cggcggcggc    60
ggcggcggcg gcggcggcgc aggggggcgc ctggccctgc tttggatagt cccgctcacc   120
ctcagcggcc tcctaggagt ggcgtggggg gcatccagtt tgggagcgca ccacatccac   180
```

<210> SEQ ID NO 2
<211> LENGTH: 60
<212> TYPE: PRT
<213> ORGANISM: Homo sapiens

<400> SEQUENCE: 2

```
Met Tyr Gln Arg Met Leu Arg Cys Gly Ala Glu Leu Gly Ser Pro Gly
  1               5                  10                  15

Gly Gly Gly Gly Gly Gly Gly Gly Gly Ala Gly Gly Arg Leu Ala
             20                  25                  30

Leu Leu Trp Ile Val Pro Leu Thr Leu Ser Gly Leu Leu Gly Val Ala
         35                  40                  45

Trp Gly Ala Ser Ser Leu Gly Ala His His Ile His
         50                  55                  60
```

<210> SEQ ID NO 3
<211> LENGTH: 180
<212> TYPE: DNA
<213> ORGANISM: Homo sapiens

<400> SEQUENCE: 3

```
atgtaccaga ggatgctccg gtgcggcgcc gagctgggct tgcccggggg cggcggcggc    60
ggcggcggcg gcggcggcgc aggggggcgc ctggccctgc tttggatagt cccgctcacc   120
ctcagcggcc tcctaggagt ggcgtggggg gcatccagtt tgggagcgca ccacatccac   180
```

<210> SEQ ID NO 4
<211> LENGTH: 60
<212> TYPE: PRT
<213> ORGANISM: Homo sapiens

<400> SEQUENCE: 4

```
Met Tyr Gln Arg Met Leu Arg Cys Gly Ala Glu Leu Gly Leu Pro Gly
  1               5                  10                  15

Gly Gly Gly Gly Gly Gly Gly Gly Gly Ala Gly Gly Arg Leu Ala
             20                  25                  30

Leu Leu Trp Ile Val Pro Leu Thr Leu Ser Gly Leu Leu Gly Val Ala
         35                  40                  45

Trp Gly Ala Ser Ser Leu Gly Ala His His Ile His
         50                  55                  60
```

<210> SEQ ID NO 5
<211> LENGTH: 180
<212> TYPE: DNA
<213> ORGANISM: Homo sapiens

<400> SEQUENCE: 5

```
atgtaccaga ggatgctccg gtgcggcgcc gagctgggct cgcccggggg cggcggcggc    60
ggcggcggcg gcggcggcgc aggggggcgc ctggccctgc tttggatagt cccgctctcc   120
ctcagcggcc tcctaggagt ggcgtggggg gcatccagtt tgggagcgca ccacatccac   180
```

<210> SEQ ID NO 6
<211> LENGTH: 60
<212> TYPE: PRT
<213> ORGANISM: Homo sapiens

<400> SEQUENCE: 6

```
Met Tyr Gln Arg Met Leu Arg Cys Gly Ala Glu Leu Gly Ser Pro Gly
1               5                   10                  15

Gly Gly Gly Gly Gly Gly Gly Gly Gly Ala Gly Arg Leu Ala
            20                  25                  30

Leu Leu Trp Ile Val Pro Leu Ser Leu Ser Gly Leu Leu Gly Val Ala
        35                  40                  45

Trp Gly Ala Ser Ser Leu Gly Ala His His Ile His
    50                  55                  60
```

<210> SEQ ID NO 7
<211> LENGTH: 18
<212> TYPE: DNA
<213> ORGANISM: Artificial
<220> FEATURE:
<223> OTHER INFORMATION: homo sapien

<400> SEQUENCE: 7

```
gcgccccaaa ctttgcct                                                  18
```

<210> SEQ ID NO 8
<211> LENGTH: 19
<212> TYPE: DNA
<213> ORGANISM: Artificial
<220> FEATURE:
<223> OTHER INFORMATION: homo sapiens

<400> SEQUENCE: 8

```
tagaaagagg ggagcgagg                                                 19
```

<210> SEQ ID NO 9
<211> LENGTH: 21
<212> TYPE: DNA
<213> ORGANISM: Artificial
<220> FEATURE:
<223> OTHER INFORMATION: homo sapiens

<400> SEQUENCE: 9

```
cttgctaatg tgcagacttg a                                              21
```

<210> SEQ ID NO 10
<211> LENGTH: 20
<212> TYPE: DNA
<213> ORGANISM: Artificial
<220> FEATURE:
<223> OTHER INFORMATION: homo sapiens

<400> SEQUENCE: 10

```
aaggaagcat ccaagaagca                                                20
```

<210> SEQ ID NO 11
<211> LENGTH: 22
<212> TYPE: DNA

```
<213> ORGANISM: Artificial
<220> FEATURE:
<223> OTHER INFORMATION: homo sapiens

<400> SEQUENCE: 11
aatggtgact agtcaactta at                                              22

<210> SEQ ID NO 12
<211> LENGTH: 20
<212> TYPE: DNA
<213> ORGANISM: Artificial
<220> FEATURE:
<223> OTHER INFORMATION: homo sapiens

<400> SEQUENCE: 12
aacggatgca aaacagtgct                                                 20

<210> SEQ ID NO 13
<211> LENGTH: 22
<212> TYPE: DNA
<213> ORGANISM: Artificial
<220> FEATURE:
<223> OTHER INFORMATION: homo sapiens

<400> SEQUENCE: 13
tcatccattg tagatataga gt                                              22

<210> SEQ ID NO 14
<211> LENGTH: 20
<212> TYPE: DNA
<213> ORGANISM: Artificial
<220> FEATURE:
<223> OTHER INFORMATION: homo sapiens

<400> SEQUENCE: 14
attgcatggc agtggctgtt                                                 20

<210> SEQ ID NO 15
<211> LENGTH: 20
<212> TYPE: DNA
<213> ORGANISM: Artificial
<220> FEATURE:
<223> OTHER INFORMATION: homo sapiens

<400> SEQUENCE: 15
ggaaatgtga gactggttgg                                                 20

<210> SEQ ID NO 16
<211> LENGTH: 23
<212> TYPE: DNA
<213> ORGANISM: Artificial
<220> FEATURE:
<223> OTHER INFORMATION: homo sapiens

<400> SEQUENCE: 16
gcccactatc ataaataata tag                                             23

<210> SEQ ID NO 17
<211> LENGTH: 20
<212> TYPE: DNA
<213> ORGANISM: Artificial
<220> FEATURE:
<223> OTHER INFORMATION: homo sapiens

<400> SEQUENCE: 17
tgagagaatc tgttaggacc                                                 20
```

```
<210> SEQ ID NO 18
<211> LENGTH: 22
<212> TYPE: DNA
<213> ORGANISM: Artificial
<220> FEATURE:
<223> OTHER INFORMATION: homo sapiens

<400> SEQUENCE: 18
ctaaggaata taacatgcaa ca                                              22

<210> SEQ ID NO 19
<211> LENGTH: 21
<212> TYPE: DNA
<213> ORGANISM: Artificial
<220> FEATURE:
<223> OTHER INFORMATION: homo sapiens

<400> SEQUENCE: 19
ttcagtgaac tcaatgatca c                                               21

<210> SEQ ID NO 20
<211> LENGTH: 20
<212> TYPE: DNA
<213> ORGANISM: Artificial
<220> FEATURE:
<223> OTHER INFORMATION: homo sapiens

<400> SEQUENCE: 20
ctctcgtcca catggtatga                                                 20

<210> SEQ ID NO 21
<211> LENGTH: 20
<212> TYPE: DNA
<213> ORGANISM: Artificial
<220> FEATURE:
<223> OTHER INFORMATION: homo sapiens

<400> SEQUENCE: 21
tcctctatgc catgtacaag                                                 20

<210> SEQ ID NO 22
<211> LENGTH: 20
<212> TYPE: DNA
<213> ORGANISM: Artificial
<220> FEATURE:
<223> OTHER INFORMATION: homo sapiens

<400> SEQUENCE: 22
ttccttcctg attgcattcc                                                 20
```